US00PP28892P2

(12) United States Plant Patent
Cornelis van Aart

(10) Patent No.: US PP28,892 P2
(45) Date of Patent: Jan. 23, 2018

(54) ***HIBISCUS* PLANT NAMED 'GANDINI VAN AART'**

(50) Latin Name: *Hibiscus syriacus*
Varietal Denomination: Gandini van Aart

(71) Applicant: Marinus Adrianus Cornelis van Aart, Oudenbosch (NL)

(72) Inventor: Marinus Adrianus Cornelis van Aart, Oudenbosch (NL)

(73) Assignee: VAN AART BOOM KWEKERIJEN, Oudenbosch (NL)

( * ) Notice: Subject to any disclaimer, the term of this patent is extended or adjusted under 35 U.S.C. 154(b) by 24 days.

(21) Appl. No.: 14/998,935

(22) Filed: Mar. 7, 2016

(51) Int. Cl.
*A01H 5/02* (2006.01)

(52) U.S. Cl.
USPC ..... Plt./257

(58) Field of Classification Search
USPC ..... Plt./257
CPC ..... A01H 5/02; A01H 5/00
See application file for complete search history.

(56) References Cited

PUBLICATIONS

New Plants and Flowers Aug. 17, 2015 White flowering version of pillar-shaped *Hibiscus syriacus*, retrieved on May 18, 2017, retrieved from the Internet at <http://www.newplantsandflowers.com/white-flowering-version-of-pillar-shaped-hibiscus-syriacus/> 2 pp.*

New Plants and Flowers Aug. 25, 2015 This years' Plantarium shows even more new varieties, retrieved on May 18, 2015,retrieved from the Internet at <http://www.newplantsandflowers.com/this-years-plantarium-shows-even-more-new-varieties/> 5 pp.*

* cited by examiner

*Primary Examiner* — June Hwu
(74) *Attorney, Agent, or Firm* — Penny J. Aguirre

(57) ABSTRACT

A new cultivar of *Hibiscus* plant named 'Gandini van Aart' that is characterized by its narrow pyramidal to pyramidal plant habit and by its semi-double flowers that are white in color and sterile.

2 Drawing Sheets

Botanical classification: *Hibiscus syriacus*.
Cultivar designation: 'Gandini van Aart'.

CROSS REFERENCE TO A RELATED APPLICATION

This application is related to a European plant breeders' rights application filed on Jun. 19, 2014, application No. 2014/1645. There have been no offers for sale anywhere in the world prior to the effective filing of this Application and no accessibility to one of ordinary skill in the art could have been derived from the printed plant breeder's rights documents.

BACKGROUND OF THE INVENTION

The present invention relates to a new and distinct cultivar of *Hibiscus* plant botanically known as *Hibiscus syriacus* 'Gandini van Aart' and will be referred to hereafter by its cultivar name, 'Gandini van Aart'. 'Gandini van Aart' is a new cultivar of hardy *hibiscus* grown for use as a landscape plant.

'Gandini van Aart' was discovered by the Inventor as a naturally occurring branch mutation of *Hibiscus syriacus* 'Gandini Santiago' (U.S. Plant Pat. No. 25,568) that was growing in a container amongst a bed of containers of 'Gandini Santiago' at a nursery in Oudenbosch, The Netherlands in August of 2012.

Asexual propagation of the new cultivar was first accomplished by softwood cuttings in Oudenbosch, The Netherlands in August of 2012 by the Inventor. Asexual propagation by grafting and softwood stem cuttings has determined that the characteristics of the new cultivar are stable and are reproduced true to type in successive generations.

SUMMARY OF THE INVENTION

The following traits have been repeatedly observed and represent the characteristics of 'Gandini van Aart'. These attributes in combination distinguish 'Gandini van Aart' as a new and distinct cultivar of *Hibiscus*.

1. 'Gandini van Aart' exhibits a narrow pyramidal to pyramidal plant habit.
2. 'Gandini van Aart' exhibits semi-double flowers that are white in color.
3. 'Gandini van Aart' exhibits sterile flowers.

'Gandini Santiago', the parent plant of 'Gandini van Aart', differs in having leaves that are lighter green in color, in having flowers that are single and pink-violet with a large red-purple eye in color. 'Gandini van Aart' can also be most closely compared to the cultivars 'Admiral Dewey' (not patented) and 'William R. Smith' (not patented). Both are similar to 'Gandini van Aart' in having white flowers. 'Admiral Dewey' differs from 'Gandini van Aart' in having a bushy and broadly upright plant habit and in having flowers that are fully double. 'William R. Smith' differs from 'Gandini van Aart' in having a bushy, broadly upright, and less pyramidal plant habit and in having only single flowers.

BRIEF DESCRIPTION OF THE DRAWINGS

The accompanying colored photograph illustrates the overall appearance and distinct characteristics of the new

*Hibiscus*. The photographs were taken of a two year-old plant of 'Gandini van Aart' as grown in a 3-liter container in an unheated greenhouse in Oudenbosch, The Netherlands.

Figure 1:
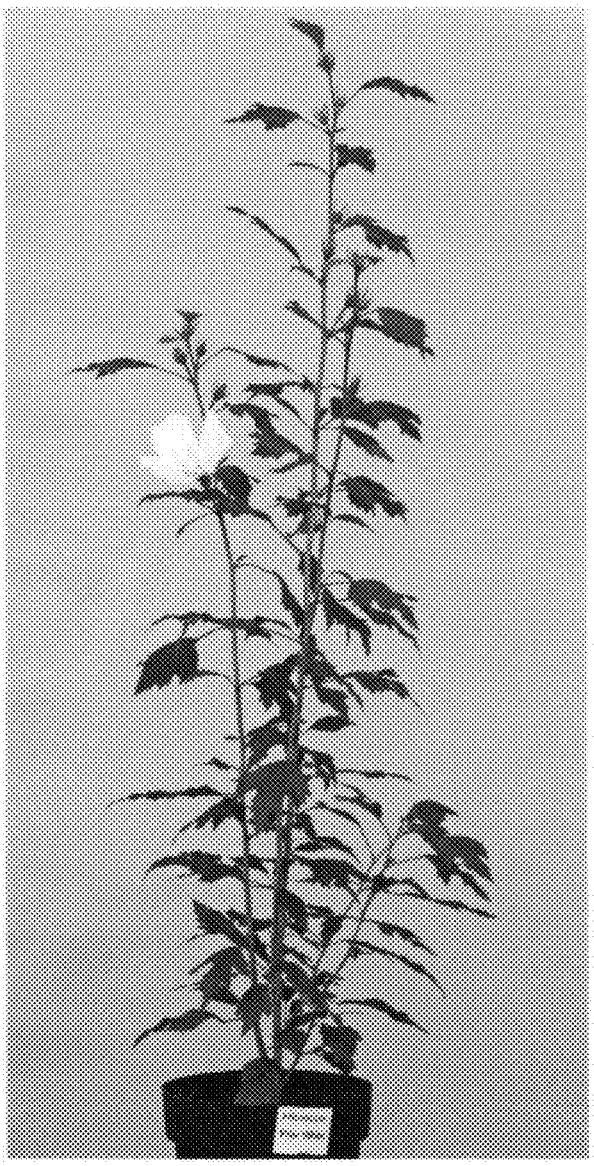

The photograph in FIG. 1 provides a side view of 'Gandini van Aart' in bloom and illustrates its pyramidal plant habit.

Figure 2:
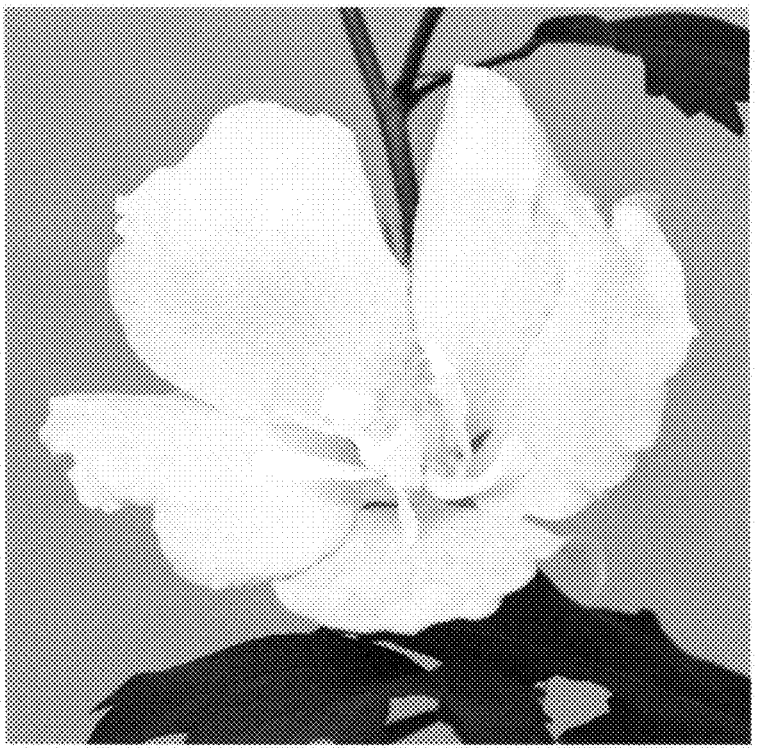

The photograph in FIG. 2 provides a close-up view of a flower of 'Gandini van Aart'.

Figure 3:
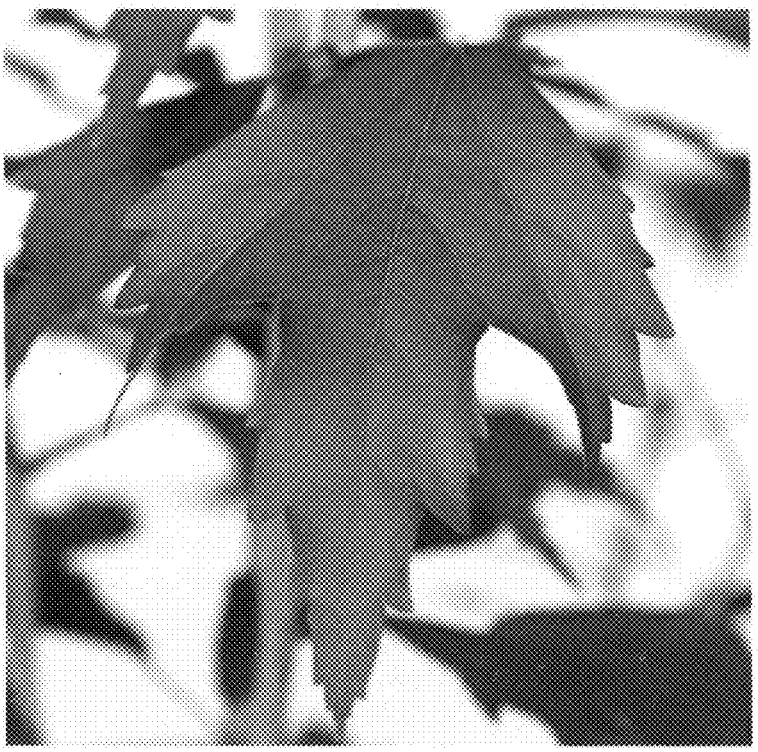

The photograph in FIG. 3 provides a close-up view of a leaf of 'Gandini van Aart'.

The colors in the photographs are as close as possible with the digital photography and printing techniques utilized and the color codes in the detailed botanical description accurately describe the new *Hibiscus*.

DETAILED BOTANICAL DESCRIPTION OF THE PLANT

The following is a detailed description of 18 month-old plants of the new cultivar as grown in a 3-liter container in an unheated greenhouse in Oudenbosch, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General characteristics:

- *Blooming period*.—Mid summer into early fall in The Netherlands.
- *Plant type*.—Herbaceous shrub.
- *Plant habit*.—Narrow pyramidal to pyramidal.
- *Height and spread*.—Reaches an average of 98 cm in height and 44 cm in width.
- *Hardiness*.—At least in U.S.D.A. Zones 5 to 9.
- *Diseases and pests*.—No susceptibility or resistance to diseases has been observed.
- *Root description*.—Fibrous.
- *Propagation*.—Softwood stem cuttings and grafting.
- *Root development*.—Cutting initiate roots in about 6 weeks and fully develop as a young rooted plant in about 3 months.
- *Growth rate*.—Moderate to high.

Stem description:

- *Shape*.—Round.
- *Stem color*.—New growth; 194A, mature wood; 197B.
- *Stem size*.—An average of 53.8 cm in length and 4 mm in diameter.
- *Stem surface*.—Glabrous.
- *Stem aspect*.—Upright, in an average angle of 70°, varying between 60° and 90° (0°=vertical).
- *Stem strength*.—Moderately strong.
- *Branching*.—Moderately free branching, an average of 5 lateral branches.
- *Internode*.—Average of 5.2 cm.

Foliage description:

- *Leaf shape*.—Overall shape is ovate, three-lobed.
- *Leaf division*.—Simple.
- *Leaf base*.—Obtuse.
- *Leaf apex*.—Narrowly acuminate.
- *Leaf venation*.—Pinnate, upper surface 137C in color, lower surface 145B in color.
- *Leaf margins*.—Coarsely crenate-serrate with leaf lobes medium in depth.
- *Leaf attachment*.—Petiolate.
- *Leaf arrangement*.—Alternate.
- *Leaf orientation*.—Held upright and slightly pendulant.
- *Leaf surface*.—Both surfaces are satiny, upper surface; glabrous, lower surface; main veins and secondary veins sparsely covered with short adpressed hairs; an average of 0.75 mm in length and NN155D in color.
- *Leaf color*.—Young leaves upper and lower surface; 144A, mature leaves upper surface; 137A to 137B, mature leaves lower surface; between 144A and 146B.
- *Leaf size*.—Average of 9.3 cm in length, and 6.1 cm in width.
- *Leaf quantity*.—About 11 leaves per lateral branch.
- *Secondary leaves*.—At each node 2 secondary leaves are present, shaped 3-lobed to elliptic, average of 5.5 cm in length and 2.7 cm in width, color and texture matches leaf blades, average length of petiole is 1.9 cm, average diameter of petiole is 1 mm, color and texture matches leaf blades.
- *Stipules*.—2 at each node, filiform in shape, 6 mm in length and 3 mm in width, glabrous surfaces, 199D in color.
- *Petioles*.—Average of 3.7 cm in length, 1.5 mm in diameter, upper side 137C in color, lower side 143A to 143B in color.

Flower description:

- *Inflorescence type*.—Flowers are solitary and semi double with the first flush of bloom and single on later blooms.
- *Lastingness of flowers*.—About 4 days, self cleaning.
- *Flower size*.—An average of 5 cm in depth and 9.8 cm in diameter.
- *Flower fragrance*.—None.
- *Flower shape*.—Rotate, semi-double or single, typical *Hibiscus* shape.
- *Flower number*.—Average of 1 per lateral stem.
- *Flower aspect*.—Outward to slightly upright.
- *Flower bud*.—Elliptic in shape, an average of 2 cm in length and 1 cm in width, color 138B, glabrous surface.
- *Flower attachment*.—Petiolate.
- *Petal number*.—Average of 5.
- *Petal shape*.—Broad obovate.
- *Petal color*.—Upper surface when opening; NN155C with base NN155B, lower surface when opening; NN155C, base a color between NN155B and 157D, upper surface when fully open; NN155D, base NN155B, lower surface when fully open; NN155C with base a color in between NN155B and 157D.
- *Petal surface*.—Both surfaces smooth, glabrous, matte, moderately velvety, base glossy.
- *Petal margins*.—Entire, slightly wavy.
- *Petal arrangement*.—Slightly overlapping.
- *Petal apex*.—Irregularly and finely repand.
- *Petal size*.—Average of 5.7 cm in length and 4.5 cm in width.
- *Petaloids*.—Present at the base of the style, 1.9 cm in length and 6 mm in width, 1.9 cm in length and 6 cm in width, average of 12, both surfaces glabrous, matte, and moderately velvety with base glossy, narrow oblong to oblanceolate in shape, entire margins, color of young and mature surfaces upper and lower surfaces; NN155C, base NN155B.

*Sepal number.*—5.
*Sepal shape*.—Elliptic to ovate.
*Sepal margin*.—Entire.
*Sepal size*.—Average of 2.1 cm in length and 8 mm in width.
*Sepal aspect*.—Rotate, lower 50% fused.
*Sepal surface*.—Both sides matte and glabrous.
*Sepal apex*.—Acute.
*Sepal base*.—Broad cuneate (fused).
*Sepal color*.—Young and mature upper surfaces; between 143C and 144B, young and mature lower surfaces; 138B.
*Calyx*.—Rotate in shape, average of 2.1 cm in length and 1.7 cm in diameter.
*Pedicels*.—Average of 3.4 cm in length, 2 mm in diameter, average angle of 30°, moderately strong, 143A in color, surfaces are glabrous.
*Bracts*.—At the base of each flower is a ring of bracts adpressed against the sepals, average of 7, linear in shape, average of 1.8 cm in length and 1.5 mm in width and 137C in color, both surfaces glabrous.
*Stipules.*—2 small filiform stipules are present at each node, an average of 6 mm in length, 0.3 mm in width and 199D in color.

Reproductive organs:
*Gynoecium*.—Pistil; 1, average of 3.8 cm in length, stigmas; club-shaped, an average of 5 and NN155A in color, style; 3.7 cm in length and NN155B in color, ovary; 145D in color and completely covered by the base of the style.
*Androecium*.—Stamens; average of 50, stamens are clustered and implanted in style, anthers; dorsifixed and broad kidney shaped, 2 mm in length and NN155D in color; filaments; 2.5 mm in length and 158B to 158C in color, pollen; abundant in quantity and 10D in color.
*Fruit/seeds*.—Sterile; no fruit or seeds are produced.

It is claimed:
1. A new and distinct cultivar of *Hibiscus* plant named 'Gandini van Aart' as herein illustrated and described.

* * * * *